United States Patent
Blackburn et al.

(10) Patent No.: US 9,518,986 B2
(45) Date of Patent: Dec. 13, 2016

(54) METHOD OF DETECTING AND/OR QUANTIFYING AN ANALYTE IN A BIOLOGICAL SAMPLE

(71) Applicant: University of Cape Town, Cape Town (ZA)

(72) Inventors: Jonathan Michael Blackburn, Cape Town (ZA); Michael Evans, Cape Town (ZA); Sriram Krishnan, Cape Town (ZA); Christa Lynn Brosseau, Halifax (CA)

(73) Assignee: University of Cape Town, Cape Town (ZA)

( * ) Notice: Subject to any disclaimer, the term of this patent is extended or adjusted under 35 U.S.C. 154(b) by 0 days.

(21) Appl. No.: 14/355,765

(22) PCT Filed: Nov. 2, 2012

(86) PCT No.: PCT/IB2012/056108
§ 371 (c)(1),
(2) Date: May 1, 2014

(87) PCT Pub. No.: WO2013/065016
PCT Pub. Date: May 10, 2013

(65) Prior Publication Data
US 2014/0302492 A1    Oct. 9, 2014

(30) Foreign Application Priority Data
Nov. 2, 2011    (ZA) .................................. 2011/08016

(51) Int. Cl.
| | | |
|---|---|---|
| *G01N 21/65* | (2006.01) | |
| *G01N 33/53* | (2006.01) | |
| *C07H 21/02* | (2006.01) | |
| *C07H 21/04* | (2006.01) | |
| *G01N 33/569* | (2006.01) | |
| *G01N 33/543* | (2006.01) | |
| *G01N 33/553* | (2006.01) | |
| *G01N 33/94* | (2006.01) | |
| *C12N 15/115* | (2010.01) | |

(52) U.S. Cl.
CPC ....... *G01N 33/56983* (2013.01); *C12N 15/115* (2013.01); *G01N 33/5438* (2013.01); *G01N 33/54353* (2013.01); *G01N 33/553* (2013.01); *G01N 33/5695* (2013.01); *G01N 33/56905* (2013.01); *G01N 33/94* (2013.01); *C12N 2310/16* (2013.01); *C12N 2310/3517* (2013.01); *C12N 2320/10* (2013.01); *G01N 2610/00* (2013.01)

(58) Field of Classification Search
None
See application file for complete search history.

(56) References Cited

U.S. PATENT DOCUMENTS

| | | |
|---|---|---|
| 5,527,712 A | 6/1996 | Sheehy |
| 7,355,704 B2 | 4/2008 | Lawandy |
| 7,432,113 B2 | 10/2008 | Koo et al. |
| 2002/0045277 A1 | 4/2002 | Schmid et al. |
| 2005/0148100 A1* | 7/2005 | Su .................... G01N 33/6818 436/523 |
| 2007/0134815 A1 | 6/2007 | Chamberlin et al. |
| 2010/0055803 A1 | 3/2010 | Lee |
| 2010/0163431 A1* | 7/2010 | Laitenberger et al. ....... 205/778 |
| 2012/0071352 A1* | 3/2012 | Liao .................... G01N 21/65 506/12 |
| 2012/0078523 A1* | 3/2012 | Letant .................. G01N 21/658 702/19 |

FOREIGN PATENT DOCUMENTS

| | | |
|---|---|---|
| JP | A06-174723 A1 | 6/1994 |
| JP | A09-222395 A1 | 8/1997 |
| JP | A2009-031023 A1 | 2/2009 |
| WO | WO 99/60157 A1 | 11/1999 |
| WO | WO 00/65352 A1 | 11/2000 |
| WO | WO 01/25758 A1 | 4/2001 |
| WO | WO 03/081230 A1 | 10/2003 |
| WO | WO 2004/074790 A1 | 9/2004 |

(Continued)

OTHER PUBLICATIONS

Cho et al (Nano Letters 8(12): 4386-4390).*
Zhang et al (Biosensors and Bioelectronics 26 (2011) 3142-3147).*
Guarrotxena et al (Chem. Commun., 2011, 47, 8784-8786).*
Jehn et al (Phys. Chem. Chem. Phys., 2009, 11, 7499-7504).*
Ochsenkühn et al (Chem. Commun., 2010, 46, 2799-2801), Su et al (US 20050148100).*
Pollet et al (Biosensors and Bioelectronics 25 (2009) 864-869).*
Hu et al., "Electrostatic Interaction Based Approach to Thrombin Detection by Surface-Enhanced Raman Spectrocopy", *Analytical Chemistry*, vol. 81, No. 1, 2009, pp. 87-93.

(Continued)

*Primary Examiner* — Richard Schnizer
(74) *Attorney, Agent, or Firm* — Myers Bigel, P.A.

(57) ABSTRACT

An aptamer-based SERS detection technique that directly monitors an aptamer-analyte capture event by generating spectroscopic information regarding the identity of the analyte that has been bound to the aptamer from a complex biological sample. A reproducible SERS spectrum is measured for an aptamer-analyte complex formed on a metal surface and this spectral information is used directly to identify the specific aptamer-analyte complex and optionally also to quantify the analyte in the sample, thus enabling discrimination between true and false positives in quantitative analyte assays on complex biological samples. In one embodiment the aptamer is attached directly to the metal surface and surrounded by a self-assembled monolayer (SAM) of amphiphilic molecules. In an alternative embodiment the metal surface is coated with a SAM and the aptamer is attached to the amphiphilic molecules of the SAM.

9 Claims, 7 Drawing Sheets

(56) References Cited

FOREIGN PATENT DOCUMENTS

| WO | WO 2005/014860 A2 | 2/2005 |
| WO | WO 2005/035791 A1 | 4/2005 |
| WO | WO 2005/066373 A1 | 7/2005 |
| WO | WO 2006/048660 A1 | 5/2006 |
| WO | WO 2006/066180 A1 | 6/2006 |
| WO | WO 2006/073439 A2 | 7/2006 |
| WO | WO 2006/076040 A2 | 7/2006 |
| WO | WO 2007/011671 A2 | 1/2007 |
| WO | WO 2007/059514 A2 | 5/2007 |
| WO | WO 2007/110614 A2 | 10/2007 |
| WO | WO 2008/116093 A2 | 9/2008 |
| WO | WO 2009/005186 A1 | 1/2009 |

OTHER PUBLICATIONS

Walter et al., "Towards a fast, high specific and reliable discrimination of bacteria on strain level by means of SERS in a microfluidic device", *Lab Chip*, vol. 11, No. 6, 2011, pp. 1013.

* cited by examiner

SEQUENCE LISTING

<160> NUMBER OF SEQ ID NOS: 7

<210> SEQ ID NO 1
<211> LENGTH: 23
<212> TYPE: DNA
<213> ORGANISM: Artificial Sequence
<220> FEATURE:
<223> OTHER INFORMATION: Anti-Mycobacterium tuberculosis DNA aptamer

<400> SEQUENCE: 1
tcctgggctg gcgggtcgct tcc                                           23

<210> SEQ ID NO 2
<211> LENGTH: 23
<212> TYPE: DNA
<213> ORGANISM: Mycobacterium tuberculosis

<400> SEQUENCE: 2
ggaagcgacc cgccagccca gga                                           23

<210> SEQ ID NO 3
<211> LENGTH: 23
<212> TYPE: DNA
<213> ORGANISM: Artificial Sequence
<220> FEATURE:
<223> OTHER INFORMATION: Scrambled DNA sequence

<400> SEQUENCE: 3
accgagccag gcagccaggg cac                                           23

<210> SEQ ID NO 4
<211> LENGTH: 36
<212> TYPE: DNA
<213> ORGANISM: Artificial Sequence
<220> FEATURE:
<223> OTHER INFORMATION: Anti-Plasmodium falciparum lactate
      dehydrogenase DNA aptamer

<400> SEQUENCE: 4
gttcgattgg attgtgccgg aagtgctggc tcgaac                             36

<210> SEQ ID NO 5
<211> LENGTH: 38
<212> TYPE: DNA
<213> ORGANISM: Artificial Sequence
<220> FEATURE:
<223> OTHER INFORMATION: Anti-Plasmodium falciparum lactate
      dehydrogenase DNA aptamer

<400> SEQUENCE: 5
gaactcattg gctggaggcg gcagtaccgc ttgagttc                           38

<210> SEQ ID NO 6
<211> LENGTH: 81
<212> TYPE: RNA
<213> ORGANISM: Artificial Sequence
<220> FEATURE:
<223> OTHER INFORMATION: Anti-gp120 RNA aptamer

<400> SEQUENCE: 6

```
gggaggacga ugcggaauug agggaccacg cgcugcuugu ugugauaagc aguuugucgu      60
gauggcagac gacucgcccg a                                                81

<210> SEQ ID NO 7
<211> LENGTH: 81
<212> TYPE: RNA
<213> ORGANISM: Artificial Sequence
<220> FEATURE:
<223> OTHER INFORMATION: Anti-gp120 RNA aptamer

<400> SEQUENCE: 7
gggaggacga ugcggacaua guaaugacac ggaggaugga gaaaaaacag ccaucucuug      60
acggucagac gacucgcccg a                                                81
```

METHOD OF DETECTING AND/OR QUANTIFYING AN ANALYTE IN A BIOLOGICAL SAMPLE

STATEMENT OF PRIORITY

This application is a 35 U.S.C. §371 national phase application of International Application Ser. No. PCT/IB2012/056108, filed Nov. 2, 2012, which claims the benefit, under 35 U.S.C. §119 (a) of South African Patent Application No. 2011/08016, filed Nov. 2, 2011, the entire contents of each of which are incorporated by reference herein.

FIELD OF INVENTION

This invention relates to biosensors, in particular to the use of Surface Enhanced Raman Scattering and aptamers for direct detection and/or quantitation of various analytes.

BACKGROUND OF INVENTION

Quantitative measurement of specific biomolecules in complex biological samples is a key component of many molecular diagnostic tests. However, the challenge of making suitable measurements across many different analyte types in a manner that is compatible with the development of low cost, rapid-readout, hand-held, battery-operated point-of-care devices remains substantial.

For example, in the infectious disease field, there is an urgent need for rapid point-of-care devices that can provide information useful in the diagnosis of diseases such as tuberculosis (TB), malaria, HIV, etc. Amongst the many limitations of current potential point-of-care diagnostic tests in the TB field (and more generally) are:

Inadequate sensitivity of assay in terms of the concentration of analyte required for detection, leading to false negative results;

Lack of specificity of detecting reagents, leading to false positive results;

Poor temperature stability of detecting reagents, leading to false negative and false positive results.

By way of illustration of such limitations, Dheda et al observed that existing antibody based Enzyme Linked Immuno Assays (ELISAs) for *Mycobacterium tuberculosis* (M. tb)-derived lipoarabinomannan (LAM), a complex glycolipid, work in urine with 99% specificity but with only 13% sensitivity, resulting in an unacceptably high false negative rate for use in the clinic.[1]

By comparison, the same test in sputum gave ~86% sensitivity but only ~15% specificity, resulting in an unacceptably high false positive rate. Dheda et al determined that the false positives in sputum are due to cross-reactivity of the anti-LAM antibodies used in the assay with LAM-like polymers produced by other microbes (both pathogenic and non-pathogenic) that co-habit the oral cavity.[1] In contrast, the false-negative results are likely due to the combination of the intrinsic antibody-antigen affinity, combined with a low antigen concentration in the biological specimen and the intrinsic limit of detection of the ELISA method. The ability to rapidly and accurately measure the concentration of specific M.tb-derived compounds such as LAM in patient specimens whilst removing false negative results (by improving the limit of detection) and false positive results (by providing direct information on the identity of the analyte that has been captured) would therefore be a major advance in TB diagnostic tests, yet it is not practically possible today.

In a different example, a major challenge in the surgical field lies in administering the correct dose of anaesthetics to patients. It is well known that individual patients metabolise the majority of drug-like molecules (including anaesthetics) at widely varying rates due to inter-individual polymorphic variations present in for example the cytochrome P450 enzymes.[2] As a consequence, the blood plasma concentrations of the active form of drugs such as anaesthetics (e.g. propofol) can vary widely between hyper- and null-metabolisers, leading in turn to variable responses to drug administration, the extreme results during surgery being either that a patient comes round during operation because the administered dose was too low for their genotype, or that the patient dies because the administered dose was too high for their genotype. In the absence of quantitative pharmacogenomic data on each individual patient that enables prior calculation of the exact optimal dose, the ability to rapidly and accurately measure and monitor the individual patient's blood plasma concentration of compounds such as propofol in real time in the operating theatre would therefore be a major advance in anaesthesiology, yet it is not practically possible.

A number of the shortcomings identified above in existing potential point-of-care diagnostic tests can be addressed through use of a novel Surface Enhanced Raman Scattering (SERS) assay platform, as described below.

Surface Enhanced Raman Scattering is a well known vibrational spectroscopy technique that has attracted considerable attention for its ultra sensitive, extremely specific and low limit of detection of biomolecules;[3] it has been reported that, compared to traditional Raman spectroscopy, the ensemble averaged Raman signal in SERS increases 8-orders of magnitude, making it able in principle to detect single molecules.[4] The SERS phenomenon utilises the intense localised evanescent wave (an electromagnetic field) that can be produced at metal surfaces and junctions by optical excitation of the surface plasmons to obtain a Raman spectrum or "signature" of surface adsorbed molecules. Classically, SERS measurements are made on individual pure compounds that are 'Raman active' and which are localised on an appropriate metal surface within the effective range of the evanescent wave. Typically a noble metal such as gold or silver is used as a SERS surface, but other transition metals such as copper iron, cobalt, nickel, palladium, and platinum can also be used.[5] Since the propagation of an evanescent wave decays exponentially with distance from the from the boundary at which the wave was formed, SERS measurements are typically made on compounds localised within 20 nm of the metal surface,[3,6] although SERS enhancement has been reported at distances up to 120 nm.[7] Importantly, because of the direct relationship of the Raman shift of incident photons to the structure of the molecule under examination, the SERS technique is highly selective and each molecule has a distinct Raman signature that is also quantifiable. Thus in principle, SERS can be used to determine the identity of a compound (by comparing the measured SERS spectrum to a database of reference SERS spectra) as well as to measure its concentration.

Detection of biomolecules (including biomarkers) by SERS could thus potentially significantly improve both the sensitivity and specificity of diagnostic assays by providing quantitative information on the identity of the molecule being detected, whilst also providing lower limits of detection. However, when applied to complex mixtures of different molecules, overlapping SERS spectra derived from the different components of the mixture makes the task of identifying and quantifying individual components in the mixture essentially impossible without some prior separation or partitioning step; this consideration has limited the application of SERS to medical diagnostics to date.

A number of studies have shown that micro-fluidics combined with SERS can be used to detect trace explosives.[8] It has also been reported that SERS can be used for various applications including detecting pollutants and DNA, whilst a SERS nano-biosensor has been designed that can accurately detect blood glucose at very low concentrations.[9,10]

Some academic groups have attempted to enhance the detection capability of SERS by combining it with aptamers as a separation and enrichment matrix for specific molecules.[11,12] Aptamers are oligonucleic acid or peptide molecules that bind to a specific target molecule and fold into 3D conformations in the presence of the target analytes.[13] In particular, DNA aptamers are highly stable nucleic acid-based polymers that can bind in a high affinity and highly discriminatory manner to proteins, nucleic acids, carbohydrates, lipids and small molecules; their molecular recognition properties thus rival and possibly exceed those of antibodies, whilst probably being more compatible than antibodies with SERS due to their smaller physical size (DNA aptamers are typically ≤100 nt in length with a molecular weight ≤35 kDa). DNA aptamers are usually generated through use of in vitro selection methods and typically show greater thermo- and humidity-tolerance than antibodies because of their smaller size, the intrinsic stability of the phosphodiester linkage, and because they typically adopt a folded conformation reversibly in response to the presence of the cognate antigen.

Cho et al[11] used an aptamer-based SERS sensor to detect thrombin. In their approach, a methylene blue-labelled anti-thrombin aptamer was first physically adsorbed to gold nano-particles; with the methylene blue-labelled aptamer in proximity to the gold surface, SERS of the methylene blue—a Raman-active dye—could occur. However, in the presence of thrombin, the anti-thrombin aptamer underwent a conformational change that weakened the physical association with the gold surface such that the aptamer-analyte complex (and hence the methylene blue label) diffused away from the surface and quenched the SERS signal. The resulting decrease in the methylene blue SERS signal was thus taken as an indirect indication of the binding of the aptamer to thrombin.[11]

In a different approach, Huh & Erickson[12] first labelled the protein vasopressin with the Raman-active dye FITC; when FITC-labelled vasopressin bound to an immobilised anti-vasopressin aptamer, the FITC label was brought into proximity of the surface, enabling the strong SERS signal of the FITC dye to be measured, thus giving indirect data on binding of vasoporessin to the aptamer.[12]

Notably, both the aptamer-SERS assays described above involve either the displacement of a Raman-labelled aptamer from a gold surface[11] or the binding of a Raman-labelled protein to an immobilised aptamer[12]. Fundamentally both methods therefore monitor movements of the Raman label rather than directly monitoring the specific aptamer-ligand capture event itself. As such, those assays provide no information about the identity of the analyte bound by the aptamer, only that something has bound, and so do not differ fundamentally in information content from existing ELISA tests or other fluorescent detection techniques.

Neumann et al[14] described the SERS-based detection of aptamer conformational changes induced by binding of the aptamer to target molecules such as proteins or organic ligands. In that work, Neumann et al demonstrated that the SERS spectrum of an unbound, thermally-denatured aptamer presented on a C6-alkyl thiol self-assembled monolayer ('SAM', 'aptamer-SAM') is reproducibly dominated by the adenine ring breathing mode of the aptamer, but noted that on binding of a specific ligand, the SERS spectrum of the aptamer-SAM became altered in an apparently poorly reproducible manner.[14] Neumann et al thus aimed to deduce the binding of a target molecule to an immobilised aptamer by measuring the aptamer-SAM SERS spectrum of the unbound, thermally-denatured aptamer-SAM and then determining the apparent loss of reproducibility of the resultant aptamer-SAM SERS spectrum that occurs on ligand binding.[14] Using circular dichroism spectroscopy, Neumann et al demonstrated for example that measurable conformational changes can be induced in an anti-cocaine aptamer-SAM by the specific target molecule cocaine, but also by the related but different molecules benzocaine and caffeine.[14] As before therefore, the SERS method of Neumann et al provides no direct spectroscopic information on the identity of the aptamer-analyte complex itself; instead Neumann et al merely infer that something has bound to the aptamer-SAM (e.g. cocaine, benzocaine or caffeine in their example) and induced an apparently poorly reproducible change in the aptamer-SAM SERS spectrum.

There remains a need for detecting and measuring the amount of a given analyte in a complex biological sample that might, for instance, also include other molecules that can cross-react with the given analyte, giving rise to false positive data in other assays.

SUMMARY OF INVENTION

In a first aspect of the present invention therefore there is provided a method of identifying an analyte molecule in a biological sample, said method involving the steps of capturing the analyte molecule onto a surface by means of an analyte-specific aptamer, measuring the SERS spectrum and SERS signal intensity of the resultant specific aptamer-analyte complex, and comparing the measured SERS spectrum to a database of reference SERS spectra to verify the identity of the captured analyte molecule.

The measured SERS signal intensity may also be compared to a standard curve to quantify the abundance of the captured analyte.

The present invention thus provides a new aptamer-based SERS detection technique that directly monitors the aptamer-analyte capture event by generating identifying and quantitative spectroscopic information regarding the identity of the analyte that has been bound to the aptamer. According to the invention, a reproducible SERS spectrum is measured for the aptamer-analyte complex formed on the surface and this spectral information is used directly to derive quantitative information about the identity of the specific aptamer-analyte complex, thus enabling true and false positives to be distinguished based on verification of the identity of the captured analyte molecule by the Raman spectrum of the aptamer-analyte complex.

The biological sample may be a complex biological sample in which the analyte is just one component of many other components.

The aptamer may be a DNA aptamer.

The analyte molecule may be a protein, a peptide, a nucleic acid, a lipid, a glycolipid, a carbohydrate, an anaesthetic, a drug, an intact cell, a bacterial pathogen or a viral pathogen. Preferably, the analyte molecule may be an analyte which is indicative of an infection, disease or medical condition in a subject or may be an anaesthetic compound or a metabolite thereof.

The surface may comprise a self-assembled monolayer (SAM) of amphiphilic molecules, and the SAM may be directly or indirectly derivatised by the aptamer molecule.

The aptamer may be attached directly to the amphiphilic molecules of the SAM, or may be attached directly to the surface and surrounded by the SAM. The SAM may be covalently coated by a layer of oligoethylene glycol molecules.

The oligoethylene glycol molecules may have exposed termini, and about 1-80% of these may be directly or indirectly derivatised by the aptamer. The aptamer may be presented above a layer of underivatised oligoethylene glycol polymers on the surface.

According to a second aspect of the invention there is provided a sensor for capturing an analyte of interest from a complex biological sample for measuring the SERS spectrum of the captured analyte, said sensor comprising a self-assembled monolayer (SAM) of amphiphilic molecules attached to a metal (e.g. gold or silver) surface of a substrate and an aptamer that is specific for the analyte of interest; wherein said SAM is coated with a layer of oligoethylene glycol molecules that are bonded to the amphiphilic molecules of the SAM.

A fraction of the amphiphilic molecules of the SAM may be directly or indirectly derivatised by an aptamer molecule.

The present invention also comprehends a detector comprising a sensor according to the invention. Suitably said detector may further comprise a laser and a SERS detector.

DETAILED DESCRIPTION OF THE INVENTION

Figure 1:
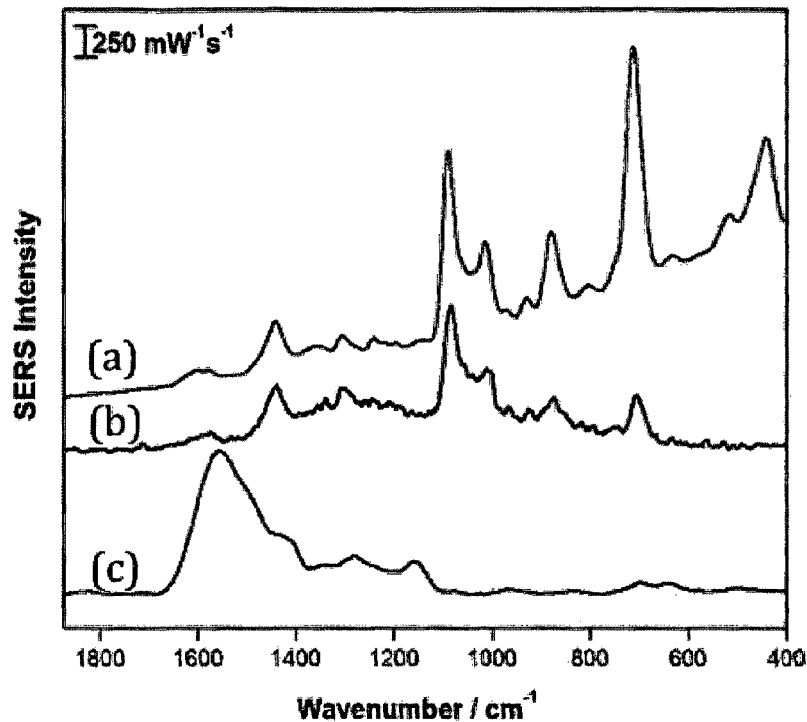
FIG. 1 shows offset SERS spectra for a 6-mercaptohexanol SAM on an AgFON surface. (a) SERS spectrum acquired immediately after SAM preparation; (b) SERS spectrum acquired 2.5 weeks after SAM preparation. Note that a 200-fold magnification of the signal relative to spectrum (a) was necessary to observe similar features; (c) SERS spectrum acquired 14 weeks after SAM preparation. Note that this represents a 10-fold magnification of the signal relative to spectrum (a).

An aptamer-based SERS detection technique is described herein which directly monitors an aptamer-analyte capture event by generating spectroscopic information regarding the identity of an analyte that has been bound to an aptamer. A reproducible SERS spectrum is measured for an aptamer-analyte complex formed on a surface and this spectral information is used directly to derive identifying and/or quantitative information about the identity of the specific aptamer-analyte complex. This enables discrimination between true and false positives in quantitative analyte assays on complex biological samples.

The analyte to be detected may be a macromolecule, for example a protein (e.g. γ-interferon, *Mycobacterium tuberculosis* 6 kDa early secretory antigen [ESAT-6], prostate specific antigen, *Plasmodium falciparum* lactate dehydrogenase, clusterin), a peptide (e.g. insulin, NMDA receptor peptide, B-type natriuretic peptide), a nucleic acid (e.g. *Mycobacterium tuberculosis* rpoB gene fragments, including drug-resistance-encoding mutated forms thereof, HIV viral RNA, *Plasmodium falciparum* genomic DNA fragments, *Salmonella typhimurium* DNA fragments, Influenza A viral RNA), a lipid (e.g. cholesterol, mycobactin, mycolic acid, phthiocerol dimycocerosate), a glycolipid (e.g lipoarabinomannan, lipopolysaccharide, sphingosine, galactosylceramide sulphate), a carbohydrate (e.g. the Thomsen-Friedenreich antigen, glucose), an anaesthetic (e.g. propofol, diazepam, thiopental, morphine, fentanyl, remifentanil, lidocaine), a drug (e.g. imatinib, gefitinib, efavirenz, rifampicin, artemesinin, methamphetamine), or may be an intact cell (e.g. *Plasmodium falciparum, Plasmodium vivax, Trypanosoma brucei*, a circulating cancer cell), a bacterial pathogen (e.g. *Mycobacterium tuberculosis, Salmonella typhimurium, Haemophilus influenza, Escherchia coli, Helicobacter pylori, Streptococcus pneumonia, Listeria monocytogenes, Vibrio cholerae*), or a viral pathogen (e.g. HIV-1, subtypes B or C, Influenza A, Hepatitis B, dengue virus, human papilloma virus). In particular embodiments, the analyte is propofol or lipoarabinomannan. In a preferred embodiment, the analyte has an intrinsic strong SERS spectrum in isolation (i.e. the analyte is itself Raman active) (e.g. glucose, lactate dehydrogenase, propofol, DNA, RNA, gefitinib, 6-thioguanine, gemcitabine, intact *Mycobacterium tuberculosis* bacilli, intact HIV-1 virions), although the method can also be performed on other analytes.

The analyte may be present in a biological sample comprising a complex mixture in which the analyte of interest is just one component of many, such as blood (including whole blood and plasma), saliva, sputum, urine, cerebrospinal fluid or stool. Identification and/or quantification of the analyte in the sample may, for example, be used to diagnose or monitor a disease, infection or medical condition (e.g. tuberculosis, malaria, HIV/AIDS), or may be used to monitor the administration of an anaesthetic to a patient.

A self-assembled monolayer (SAM) is an organised layer of amphiphilic molecules in which one end of the molecule, the "head group", shows a special affinity for a surface.[15] Typically, in the SAM of the invention, the surface may be a metal such as gold, silver, copper, iron, cobalt, nickel, palladium, or platinum, and the head group may be a thiol. Preferably, the surface may be gold or silver nano-particles, or may be gold or silver film coated nano-spheres.

In addition to the head group, the amphiphilic molecules of the SAM also comprise a hydrophobic tail which may have a functional group at the terminal end. Examples of the functional group include an N-hydroxysuccinimide ester, an epoxide, an amine, a carboxylate, a hydrazide, or an aminooxy group. On binding of the head group to the surface, the hydrophobic tails of the amphiphilic molecules undergo a slow 2D self-organisation. The hydrophobic tail may typically be an alkyl chain, with a length typically from about 6 to about 16 carbons. For example, the alkyl chain may have a length of 6, 7, 8, 9, 10, 11, 12, 13, 14, 15 or 16 carbons. The degree of ordering in the resultant SAM is dependent on a number of factors, including the length of the alkyl chain—the longer the alkyl chain, the greater the degree of organisation and the greater the stability of the SAM. Well-formed SAMs typically show high stability over temperature, solvents and potentials. Well-formed SAMS can, for example, be prepared from solutions of 11-mercaptoundecanol, 12-mercaptododecanoic acid, or 16-mecaptohexadecanoic acid, but other reagents for preparing SAMS are well known in the art.

The functional group may be chemically derivatised using a range of molecules, including, but not limited to, DNA-, RNA-, or peptide-aptamers targeted for the specific analyte of interest, as well as polymers that resist the non-specific absorption of macromolecules. Examples of polymers include ethylene glycol polymers, ethylene imine polymers, hyaluronic acid, or carboxymethyl dextran. Such chemical derivatisations are typically carried out after formation of the SAM, but in some embodiments it is possible to chemically derivatise the amphiphilic molecules prior to SAM formation.[15]

The SAM may be covalently coated by a layer of oligoethylene glycol molecules. Said oligoethylene glycol polymers may suitably be 3 to 12 ethylene glycol units in length (such as 3, 4, 5, 6, 7, 8, 9, 10, 11 or 12 units in length) and may be bonded to the functional groups on the tails of the amphiphilic molecules that form the SAM. For example, 2-{2-[2-(1-mercaptoundec-11-yloxy)-ethoxy]-ethoxy}-ethanol (HS—$(CH_2)_{11}$—$(OC_2H_4)_3$—OH; 1-mercaptoundecanyl-11-tri(ethyleneglycol); HS—C11-EG3), 2-(2-{2-[2-(1-mercaptoundec-11-yloxy)-ethoxy]-ethoxy}-ethoxy)-ethanol (HS—C11-EG4), 2-{2-[2-(2-{2-[2-(1-mercaptoundec-11-yloxy)-ethoxy]-ethoxy}-ethoxy)-ethoxy]-ethoxy}-ethanol (HS—C11-EG6), 11-{2-[2-(2-methoxy-ethoxy)-ethoxy]-ethoxy}-undecane-1-thiol (HS—$(CH_2)_{11}$—$(OC_2H_4)_3$—$OCH_3$; HS—C11-EG3-OMe), or 11-{2-[2-(2-{2-[2-(2-methoxy-ethoxy)-ethoxy]-ethoxy}-ethoxy)-ethoxy]-ethoxy}-undecane-1-thiol (HS—C11-EG6-OMe) may be used to form stable SAMs that are covalently coated by a layer of oligoethylene glycol molecules.

In some embodiments, an oligoethylene glycol-terminated, alkyl thiol-based SAM may be assembled on a surface made of silver or gold nano-particles, or on a surface made of silver or gold film coated nano-spheres.

Suitably, the aptamer may derivatise the oligoethylene glycol-terminated SAM such that a fraction, suitably about 1-80%, of the underlying amphiphilic molecules that form the SAM are directly or indirectly derivatised by an aptamer molecule. In some embodiments, more than about 2%, about 5% or about 10% and less than about 70%, about 60% or about 50% of the underlying amphiphilic molecules that form the SAM may be directly or indirectly derivatised by an aptamer molecule.

Some or all of the oligoethylene glycol molecules may be derivatised on their exposed termini by the aptamer that is specific for the analyte of interest.

Alternatively, the aptamer may be attached directly to the amphiphilic molecules of the SAM.

In some embodiments, the aptamer may be presented above a layer of underivatised oligoethylene glycol polymers.

In other embodiments, the aptamer may be attached directly to the surface and may optionally be surrounded by an oligoethylene glycol-terminated SAM.

The aptamer may suitably be a DNA, RNA or peptide aptamer which is specific for the analyte of interest. The aptamer may be a previously described aptamer (if available) or may be identified through processes which are well known in the art, such as in vitro selection or SELEX (systematic evolution of ligands by exponential enrichment) utilising an immobilised analyte molecule for the enrichment steps, described in U.S. Pat. Nos. 5,475,096 and 5,843,653. It will be obvious to a person skilled in the art that an aptamer for an analyte of interest does not need to be limited to an oligonucleotide having the particular sequences which are described in the examples below.

In accordance with the present invention, the aptamer-oligoethylene glycol-SAM surface is contacted with a sample containing the analyte, allowing an aptamer-analyte complex to form on the surface, after which the surface may optionally be washed to remove unbound material and a variable voltage may optionally be applied to the surface. The SERS spectrum and SERS signal intensity of the resultant aptamer-analyte complex are then measured. The identity of the captured analyte can then be determined by comparison of the measured SERS spectrum to a reference database of SERS spectra. The amount of the analyte in the original sample can be determined by comparison of the measured SERS signal intensity to a standard curve.

The aptamer-functionalised SAM acts as a partition layer, enabling the analyte to be captured and enriched close enough to the silver film such that sufficient plasmon resonance-based excitation of the aptamer-analyte complex can take place, yielding a strong SERS signal from the aptamer-analyte complex. Suitably the functionalised SAM (for example, an oligoethylene glycol-terminated SAM) may also reduce non-specific macromolecule absorption to the surface—as well as to the SAM itself—thereby reducing the background signal in downstream SERS spectra, hence improving signal-to-noise ratios. In accordance with the present invention, an aptamer-functionalised SAM that minimises the physical interaction between the aptamer and the SAM surface by presenting the aptamer above a layer of oligoethylene glycol molecules—while maintaining the aptamer within the effective range of the evanescent wave of the surface—results, on binding of the analyte by the aptamer, in reproducible, unique SERS spectra for the specific aptamer-analyte complex, thus enabling the identity of the analyte that has bound to the aptamer to be determined, as well as enabling the amount of analyte present in the sample to be determined.

For real-time monitoring of an analyte such as an anaesthetic, the aptamer must be chosen to allow reversible binding/partitioning of the analyte on a timescale appropriate to the frequency of measurements required. This can be achieved by use of an anti-analyte aptamer that has a binding affinity ($K_d$) in the micro- to nanomolar range, such that the half-life ($t_{1/2}$) of dissociation of the analyte from the aptamer-analyte complex is on the timescale of minutes rather than hours.

Figure 10:
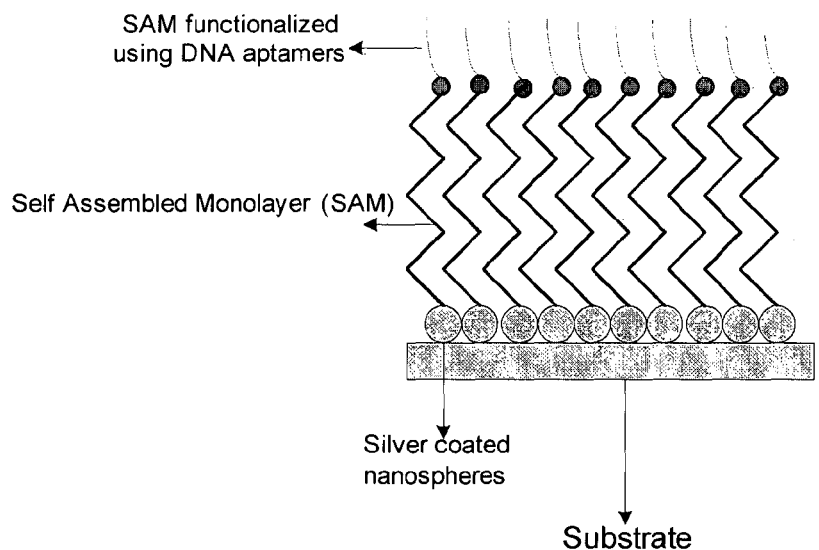
FIG. 10 is a schematic of an aptamer-functionalised SAM-derivatised AgFON SERS sensor surface.
Figure 11:
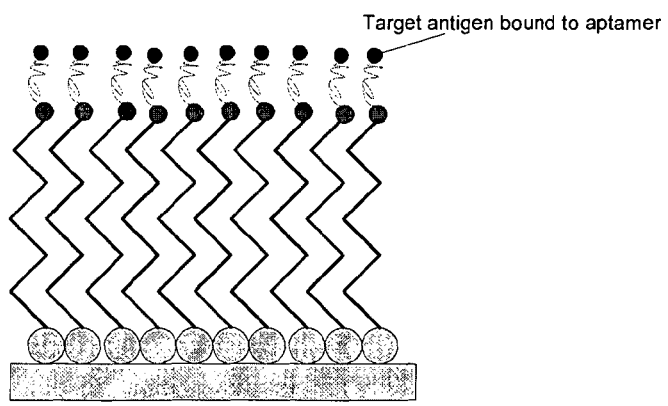
FIG. 11 is a schematic depicting that aptamer-analyte complexes on aptamer-functionalised SAM-derivatised AgFON surfaces having reproducible 3D structures.
Figure 12:
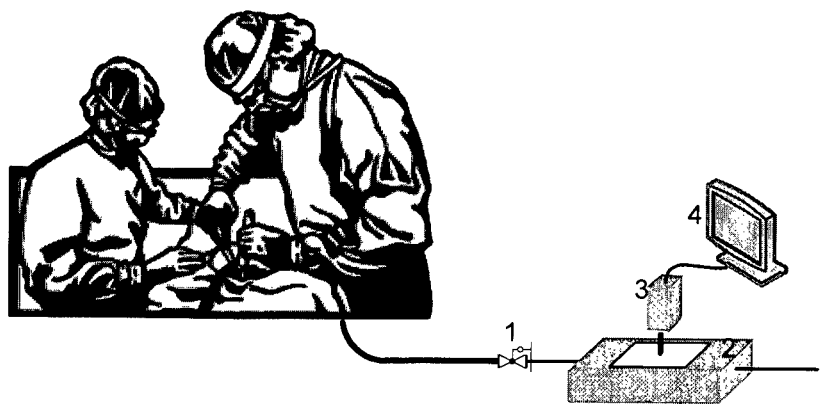
FIG. 12 is a schematic of the setup of a SERS bio sensor for real time monitoring of the blood plasma concentration of an anaesthetic.
Figure 13:
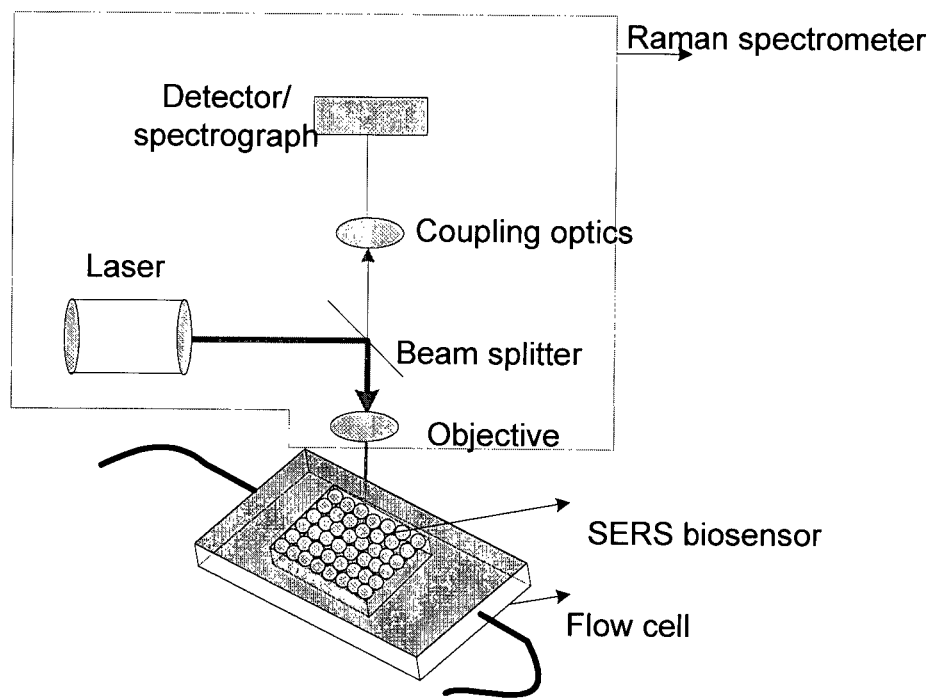
FIG. 13 is a schematic of a SERS biosensor placed in a flow cell.
Figure 14:
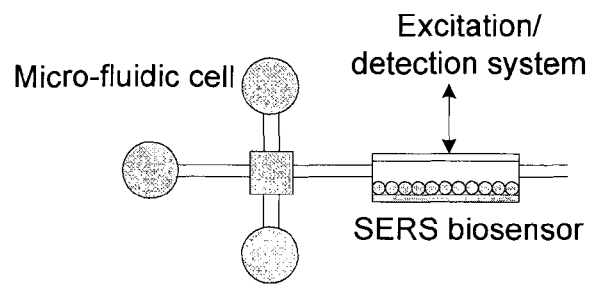
FIG. 14 is a schematic of a micro-fluidic system attached to a SERS biosensor.
Figure 15:
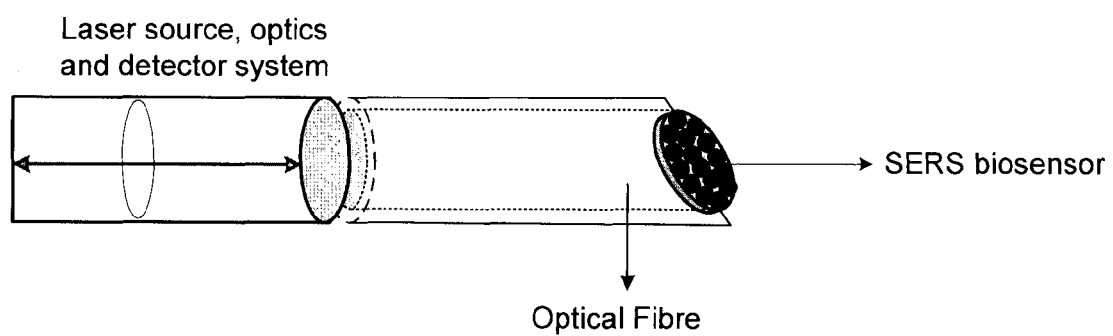
FIG. 15 is a schematic of a fibre optic probe with a SERS sensor on the tip.

FIG. 10 depicts such a functionalised biosensor surface and represents the aptamers to be in an unfolded state. When the SERS biosensor is brought in contact with the target analyte, the aptamers typically undergo a conformational change to adopt an 'active' conformation able to bind the analyte molecule with high affinity and specificity, as depicted in FIG. 11.

The SERS spectrum of aptamer-analyte complex on the sensor surface of the invention arises due to unique vibrational modes in the captured analyte and in the analyte-bound aptamer. Thus, the SERS spectrum of the aptamer-analyte complex will differ from the SERS spectrum of either aptamer or analyte in isolation.

In a preferred embodiment, the precise nucleotide sequence of a DNA aptamer together with the precise and reproducible 3-dimensional shape of the aptamer-analyte complex gives rise to unique polarisability and hence vibrational modes for the specific aptamer-analyte complex, resulting in the aptamer-analyte complex having a measurable and unique SERS signature, irrespective of whether the analyte itself has a strong SERS signature or not.

The excitation wavelength of the Raman sensor may be tuned to be optimal for each specific aptamer-analyte complex. Fourier transform methods may also be used to deconvolute SERS spectra obtained on illumination of the nanoparticles with a broad spectrum light source.

The method and the sensor of the invention thus work both in the case where the analyte molecule to be detected has an intrinsic strong SERS spectrum in isolation (e.g. glucose, lactate dehydrogenase, propofol, DNA, RNA, gefitinib, 6-thioguanine, gemcitabine, intact *Mycobacterium tuberculosis* bacilli, intact HIV-1 virions) and where the analyte molecule to be detected does not have an intrinsic strong SERS spectrum in isolation (e.g. ESAT-6, γ-interferon, insulin).

An important feature of the invention is the ability to produce reproducible SERS spectra for each aptamer-analyte complex. This is achieved in one embodiment of the invention by providing a well-formed (i.e. highly organised), stable SAM on a metal surface, coating said well-formed SAM with a layer of polymers that resist non-specific macromolecule absorption, and further derivatising a fraction of said well-formed SAM with an aptamer. Thus, on capture of a specific analyte by said aptamer, the polymer layer that resists non-specific absorption of macromolecules to the SAM surface of the invention also serves to minimise non-specific, non-covalent interactions between the resultant aptamer-analyte complexes and the SAM surface, as well as to minimise the extent to which the resultant aptamer-analyte complexes are able to bury into or through the SAM. This is important because non-specific, non-covalent interactions between the aptamer-analyte complexes and the SAM surface, as well as any burying of the aptamer-analyte complexes into or through the SAM surface, have the capacity to distort the SERS spectrum of the aptamer-analyte complex in a poorly reproducible manner. In the absence of such distortions, the SERS signature of a specific aptamer-analyte complex thus uniquely and reproducibly represents the relevant aptamer-ligand capture event and by doing so provides quantitative information on the exact identity of the analyte of interest.

Alternatively, the ability to produce reproducible SERS spectra for each aptamer-analyte complex may be achieved in another embodiment of the invention by functionalising the metal surface directly with an aptamer and then surrounding the immobilised aptamer with a well-formed SAM that resists non-specific macromolecule absorption. On capture of a specific analyte by said aptamer, the surrounding SAM serves to minimise non-specific, non-covalent interactions between the resultant aptamer-analyte complexes and the SAM surface, as well as to minimise the extent to which the resultant aptamer-analyte complexes are able to bury into or through the SAM. The SAM also serves to resist non-specific absorption of macromolecules to the SAM surface of the invention.

The method of the invention does not make use of an indicator reagent. The method can also be performed without the use of a structure to split an optical beam into a plurality of optical beams and without use of an apparatus which contains a low resolution diffraction grating dispersion element to receive and separate scattered radiation into different wavelength components.

Preferred features of each aspect of the invention are as defined for each other aspect, *mutatis mutandis*.

Further features and details of the invention will be apparent from the following non-limiting examples.

EXAMPLES

1. Preparation and Analysis of Self-assembled Monolayer-derivatised SERS Sensor Surfaces To prepare a self-assembled monolayer (SAM) derivatised SERS sensor surface, a glass cover slip was cleaned in pyrannah solution and washed in deionised water. 600 nm silica particles were suspended at 5% (w/v) in deionised water and were then drop coated on to the cover slip. The resultant close packed silica particles on the glass cover slip were then inserted into a vapour deposition chamber and 200 nm silver was deposited at a rate of 0.24 nm s$^{-1}$ to form a silver film over nanoparticles (AgFON) surface suitable for SERS, essentially as described.[3] Replica AgFON surfaces were then submerged in a either 6-mercaptohexanol solution (1 mM solution in ethanol) or a 12-mercaptododecanoic acid solution (1 mM solution in ethanol; catalog number 705241, Sigma Aldrich) and incubated overnight at room temperature to allow the respective self-assembled monolayers to form on the nanostructured silver surfaces. After incubation, the SAM-derivatised AgFON surface was rinsed repeatedly with ethanol.

Figure 2:
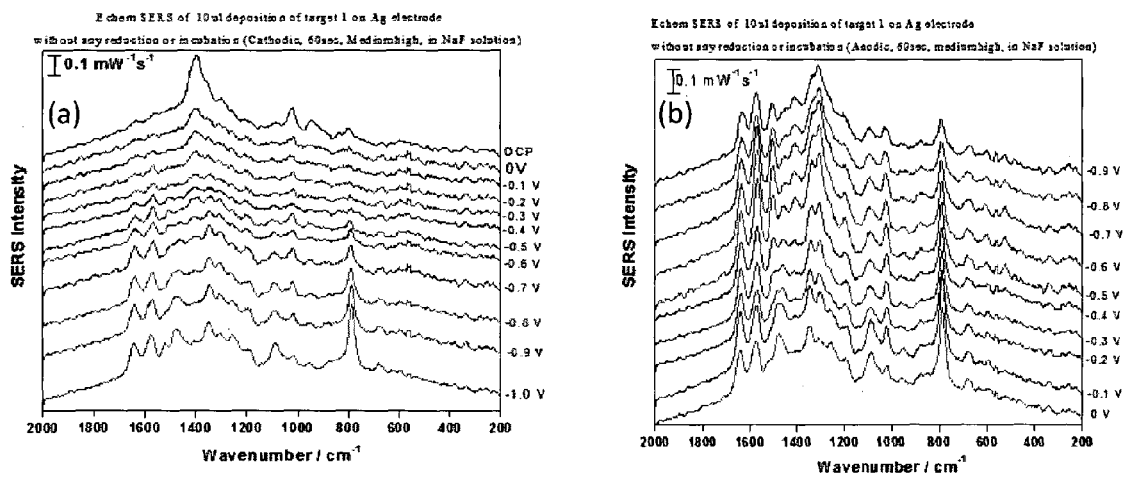
FIG. 2 shows SERS spectra for an Oligo 1-functionalised AgNP surface. (a) offset SERS spectra acquired at varying cathodic potentials as indicated on the Y-axis; (b) offset SERS spectra subsequently acquired at voltages stepped anodically, as indicated on the Y-axis.

Following preparation of the SAMs on the nanostructured silver surfaces, the stability of the SAMs was monitored by SERS periodically over a 14 week period using a DeltaNu benchtop dispersive Raman spectrometer (air-cooled CCD, 785 nm diode laser). These SERS assays clearly showed that within a period of 2.5 weeks, the 'C6 SAM' (i.e. the SAM formed using 6-mercaptohexanol) had substantially degraded (FIG. 1). However, the SERS spectrum of the 'C12 SAM' (i.e. the SAM formed using 12-mercaptododecanoic acid) (FIG. 2) was observed to be stable over the same time period (data not shown).

These data are in accord with the expectation based on the literature that longer chain SAMs should be more stable. It is noteworthy therefore that in the prior art, Neumann et al immobilised a DNA aptamer on a silver surface via a C6-linker and observed poorly reproducible SERS spectra for the aptamer, probably due to formation of an incomplete, heterogeneous and unstable SAM.

2. Preparation and Analysis of a DNA-functionalised, Colloidal Silver SERS Sensor Surface A boiling solution of 1 mM silver nitrate (500 ml; >99.9% purity) was reduced by addition of a 1% (w/v) sodium citrate solution (10 ml; >99.5% purity) to create a silver nanoparticle (AgNP) colloid (expected NP diameter between 30 and 60 nm). After boiling for 30 minutes, the colloidal silver NPs were collected by centrifugation (3,600×g; 15 mins) and then drop coated onto the carbon paint working electrode of commercially available screen printed electrodes (SPE) in three 5 µL aliquots, after which the electrodes were allowed to dry completely, creating an AgNP surface suitable for SERS.

A 5'-thiol terminated DNA oligonucleotide (Oligo 1; 5'-HS—$(CH_2)_6$-TCC TGG GCT GGC GGG TCG CTT CC-3' (SEQ ID NO: 1)) in disulphide form was resuspended in 50 mM $Na_2PO_4$ pH7.4 to a concentration of 2 mM and incubated overnight with the AgNP surface in order to immobilise the oligonucleotide on to the nanostructured silver surface via the 5'-thiol group; reduction of the disulphide bond to free thiols occurred spontaneously in situ.

The DNA-functionalised, colloidal silver SERS sensor surface on the SPE was then inserted into an electrochemical cell consisting of a glass voltammetry cell with a mini-USB adapter that held the screen printed electrode. The electrode was coupled to a potentiostat and electrochemical SERS measurements were then made on the immobilised oligonucleotide at varying cathode potentials, stepping the applied potential in the cathodic direction from 0.0V to −1.0V in 100 mV increments. The screen printed electrodes featured a built-in counter electrode (carbon) and reference electrode (Ag/AgCl) and all potentials were measured vs Ag/AgCl. SERS spectra were obtained using a DeltaNu benchtop dispersive Raman spectrometer (air-cooled CCD, 785 nm diode laser) at medium-high power (46.5 mW) and with a 30 second acquisition time. The resultant SERS spectra clearly showed that the DNA oligonucleotide had immobilised onto the silver NP surface and also showed that the SERS signal intensity of the DNA-functionalised AgNP surface could be tuned by altering the cathodic potential to negative potentials vs Ag/AgCl such that the SERS spectrum of the immobilised DNA oligonucleotide was no longer dominated by the spectrum of citrate (FIG. 2a). When the voltage was subsequently stepped anodically, the SERS spectrum of the DNA-functionalised AgNP surface was retained (FIG. 2b).

Figure 3:
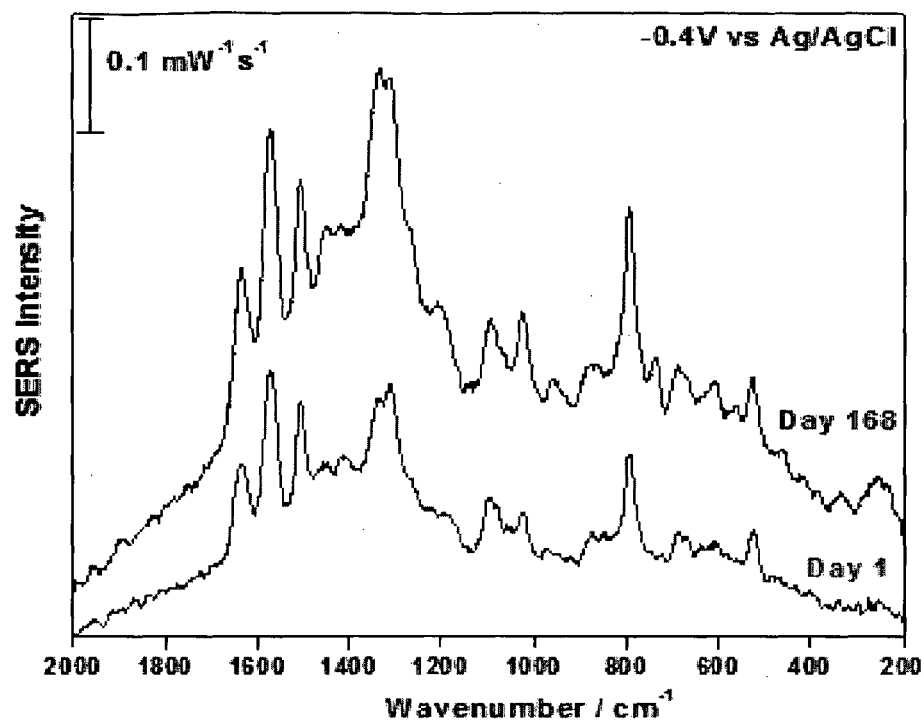
FIG. 3 shows two offset SERS spectra aquired at 6 month intervals on the same Oligo 1-functionalised AgNP surface. These spectra were acquired at −0.4V relative to Ag/AgCl.

SERS spectra of the immobilised DNA oligonucleotide were then recorded periodically over a period of 6 months, during which time no noticeable degradation in signal was observed (FIG. 3) suggesting that the DNA-functionalised, colloidal silver SERS sensor surface is stable.

Figure 4:
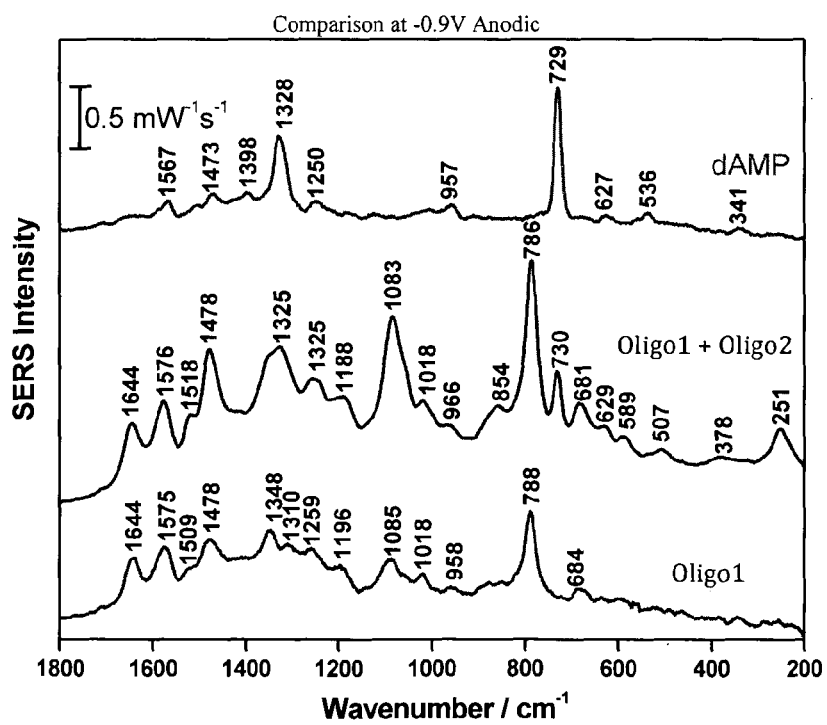
FIG. 4 shows offset SERS spectra of an Oligo 1-funtionalised AgNP surface acquired before and after binding of Oligo 2. For reference, a SERS spectrum of deoxyadenosine monophosphate on an AgNP surface is also shown offset.

3. Label-free Detection of *Mycobacterium tuberculosis* DNA Fragments Using a DNA-functionalised, SAM-derivatised SERS Sensor Surface Replica DNA-functionalised, colloidal silver SERS sensor surfaces (prepared according to Example 2 using Oligo 1) were incubated with either a complementary DNA oligonucleotide (Oligo 2; 5'-GGA AGC GAC CCG CCA GCC CAG GA-3' (SEQ ID NO: 2); 2 mM in 50 mM $Na_2PO_4$ pH7.4) or a scrambled sequence DNA oligonucleotide (Oligo 3; 5'-ACC GAG CCA GGC AGC CAG GGC AC-3' (SEQ ID NO: 3); 2 mM in 50 mM $Na_2PO_4$ pH7.4) for 1 hour at room temperature to allow DNA hybridisation to occur. SERS spectra were then recorded for each DNA-functionalised, SAM-derivatised SERS sensor surface as per Example 2. The resultant spectra showed that hybridisation of Oligo 2 (which sequence is derived from the IS6110 genomic DNA sequence of *Mycobacterium tuberculosis* and which is perfectly complementary to the sequence of immobilised Oligo 1) to immobilised Oligo 1 could be detected in a label-free and amplification-free manner by SERS (FIG. 4).

Figure 5:
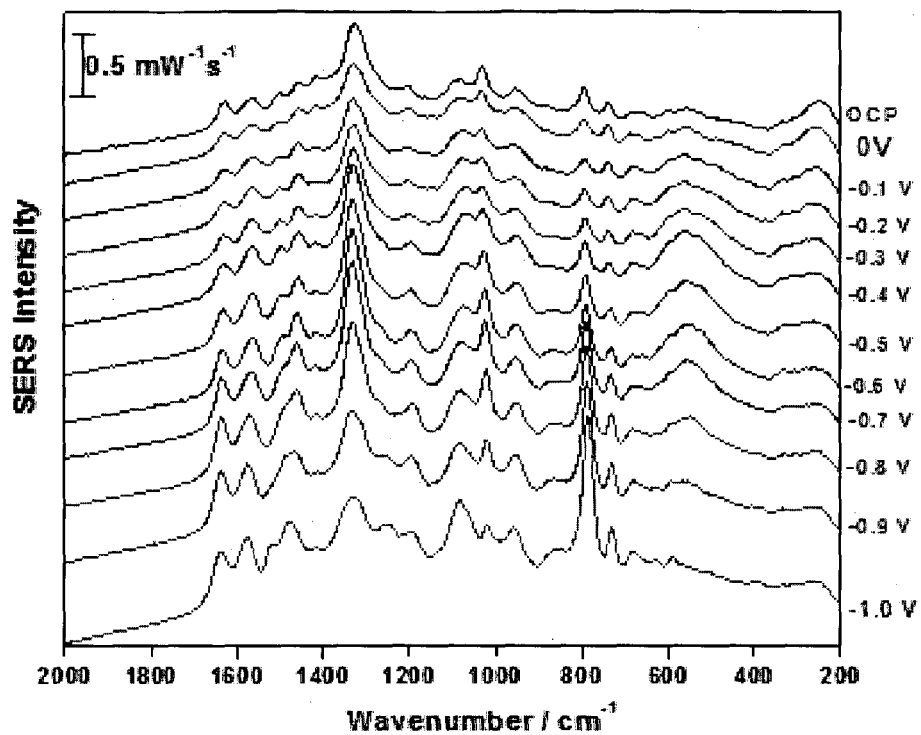
FIG. 5 shows SERS spectra of an Oligo 1-funtionalised AgNP surface acquired after binding of scrambled Oligo 3. The offset spectra were acquired at varying cathodic potentials relative to Ag/AgCl, as indicated on the Y-axis.

However, the SERS spectra also showed that non-specific binding of Oligo 3 could be observed, presumably as a result of direct physisorption of Oligo 3 to the AgNP surface (FIG. 5).

In order to abrogate this non-specific binding, a DNA-functionalised, colloidal silver SERS sensor surface (prepared according to Example 2 using Oligo 1) was incubated in a 12-mercaptododecanoic acid solution (1 mM solution in ethanol) overnight at room temperature in order to allow a self-assembled monolayer (SAM) to form, back-filling on the nanostructured silver surface; this 'C12 SAM' surrounded but not did not displace the previously immobilised molecules of Oligo 1, thus creating a DNA-functionalised, SAM-derivatised AgNP surface suitable for SERS.

Replica DNA-functionalised, C12 SAM-derivatised colloidal silver SERS sensor surfaces were then incubated with either Oligo 2 or Oligo 3 (DNA concentrations and buffers as before) for 1 hour at room temperature to allow DNA hybridisation to occur. SERS spectra were then recorded for each DNA-functionalised, SAM-derivatised SERS sensor surface as above. The resultant spectra showed that sequence-specific hybridisation of Oligo 2 to immobilised Oligo 1 could be detected in a label-free and amplification-free manner by SERS (FIG. 6a; note the peaks at ~730 cm$^{-1}$ and ~1328 cm$^{-1}$ that are characteristic of the hybridised oligonucleotide) but that non-specific binding of Oligo 3 could no longer be observed (FIG. 6b; note the absence of peaks at ~730 cm$^{-1}$ and ~1328 cm$^{-1}$), presumably because the C12 SAM now prevented physisorption of Oligo 3 to the AgNP surface. Furthermore, the SERS spectrum of Oligo 2 hybridised to immobilised Oligo 1 on the DNA-functionalised, C12 SAM-derivatised colloidal silver SERS sensor surfaces was observed to be reproducible across replica experiments and replica sensor surfaces. In addition, equivalent SERS spectra could be recorded for the hybridisation of Oligo 2 to immobilised Oligo 1 where the hybridisation was performed in urine or urine-like buffers, indicating that other inorganic molecules (e.g. chloride ions) or biomolecules (e.g. any non-complementary transrenal DNA fragments) present in urine do not interfer with the SERS assay on such DNA-functionalised, C12 SAM-derivatised colloidal silver SERS sensor surfaces.

Figure 6:
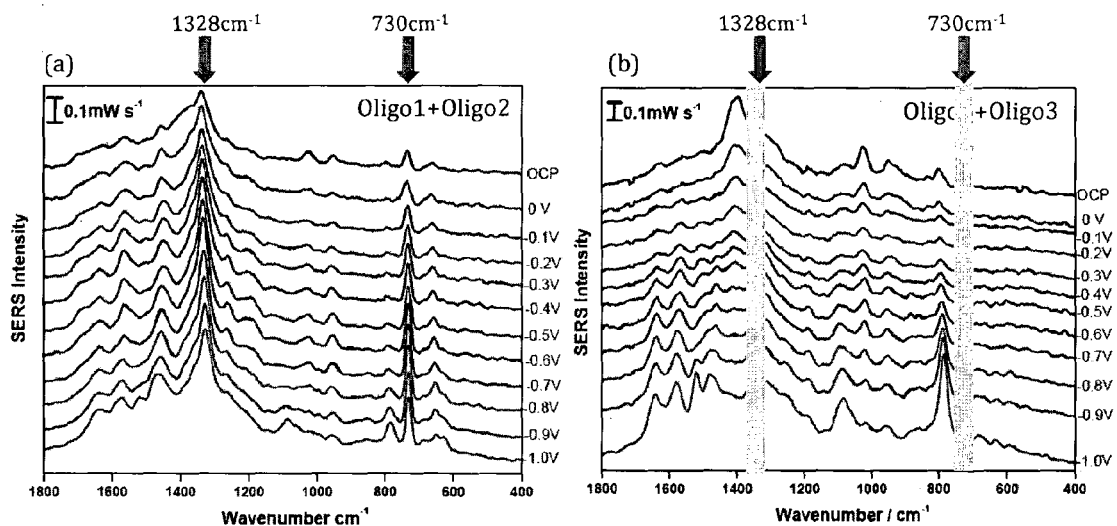
FIG. 6 shows SERS spectra of Oligo 1-funtionalised, C12-SAM-derivatised AgNP surface aquired at varying cathodic potentials relative to Ag/AgCl, as indicated on the Y-axis. (a) offset SERS spectra acquired after incubation with complementary Oligo 2; offset SERS spectra acquired after incubation with scambled Oligo 3.

Using this DNA-functionalised, C12 SAM-derivatised colloidal silver SERS sensor system, it was observed that by stepping the cathodic voltage to negative potentials relative to Ag/AgCl, the intensity of the SERS spectrum resulting from the specific hybridisation of Oligo 2 to Oligo 1 could be increased by 3-5 fold but that the distribution of peaks in the SERS spectrum did not alter in the process (FIG. 6a).

This Example demonstrates the ability to obtain a reproducible SERS spectrum of a DNA aptamer-analyte binding event on a SAM-derivatised surface according to the present invention. The combination of immobilised DNA oligonucleotides with well formed, stable SAMs on nanostructured silver surfaces enables the homogeneous presentation of the immobilise DNA oligonucleotides such that they are able to selectively bind the analyte of interest (in this case, a complementary DNA oligonucleotide) in close proximity to the surface, resulting in a stronger, reproducible SERS signal. Furthermore, the SAM also serves to reduce non-specific macromolecule absorption to the nanostructured silver surface, thereby improving signal-to-noise ratios in downstream SERS spectra as also required for biosensor applications.

4. Detection of *Plasmodium falciparum* Lactate Dehydrogenase Using a DNA Aptamer-functionalised, SAM-derivatised SERS Sensor Surface DNA-functionalised, SAM-derivatised colloidal silver SERS sensor surfaces were prepared on screen printed electrodes essentially as described in Example 3, with the following differences: an in vitro selected 5'-thio-anti-*Plasmodium falciparum* lactate dehydrogenase DNA aptamer[17] (Aptamer 4; 5'-HS—(CH$_2$)$_6$-GTT CGA TTG GAT TGT GCC GGA AGT GCT GGC TCG AAC-3' (SEQ ID NO: 4); 2 mM in 50 mM Na$_2$PO$_4$ pH7.4) was used in place of Oligo 1; and 1-mercaptoundecanyl-11-tri(ethyleneglycol) (HS—(CH$_2$)$_{11}$—(OC$_2$H$_4$)$_3$—OH; HS—C11-EG3; ProChimia Surfaces, Poland) (1 mM in ethanol) was used in place of 12-mercaptododecanoic acid.

Recombinant *Plasmodium falciparum* lactate dehydrogenase (pfLDH; 1 µg/ml in 10 mM HEPES pH7.5) is incubated for 30 minutes on an Aptamer 4-functionalised, C11-EG3-SAM-derivatised AgNP surface, the surface then washed with 3×1 ml 10 mM HEPES pH7.5 to remove unbound pfLDH and SERS spectra recorded as before. The recorded spectrum are then compared to a database of reference SERS spectra to confirm the identity of the captured biomolecule.

In this Example, the oligoethylene glycol-terminated C11 SAM provides increased resistance to non-specific macromolecule adsorption onto the sensor surface, whilst the DNA aptamer provides specific recognition of the pfLDH protein; the combination of these enables the measurement of reproducible SERS spectra for the resultant aptamer-analyte complex, including where pfLDH is captured by an aptamer from a blood or plasma sample obtained from a patient with suspected malaria.

Since in vitro selection procedures to produce analyte-specific aptamers typically identify several unique nucleic acid sequences that are capable of selectively and tightly binding the target analyte, it is also possible to use alternative in vitro selected 5'-thio-anti-*Plasmodium falciparum* lactate dehydrogenase DNA aptamers, for example 5'-HS—(CH$_2$)$_6$-GAA CTC ATT GGC TGG AGG CGG CAG TAC CGC TTG AGT TC-3' (SEQ ID NO: 5),[17] in place of Aptamer 4 for the SERS-based detection of *Plasmodium falciparum* lactate dehydrogenase.

5. Detection of Viral Pathogens Using an RNA Aptamer-functionalised, SAM-derivatised SERS Sensor Surface RNA-functionalised, SAM-derivatised colloidal silver SERS sensor surfaces are prepared on screen printed electrodes essentially as described in Example 4, with the following amendment: a 5'-thio-anti-gp120 RNA aptamer (Aptamer 5; 5'-HS—(CH$_2$)$_6$-GGG AGG ACG AUG CGG AAU UGA GGG ACC ACG CGC UGC UUG UUG UGA UAA GCA GUU UGU CGU GAU GGC AGA CGA CUC GCC CGA-3' (SEQ ID NO: 6))[18] is used in place of the anti-*Plasmodium falciparum* lactate dehydrogenase DNA aptamer; as before, 1-mercaptoundecanyl-11-tri(ethyleneglycol) was used to form the back-filled SAM surrounding the immobilised RNA aptamer. Note that in Aptamer 5, all cytosine (C) and uracil nucleosides are replaced with 2'-deoxy-2'-fluoro-cytosine and with 2'-deoxy-2'-fluoro-uracil respectively to provide nuclease resistance.[18]

A suspension of intact HIV pseudovirus is incubated for 30 minutes on an Aptamer 5-functionalised, C11-EG3-SAM-derivatised AgNP surface, the surface then washed with 3×1 ml 10 mM HEPES pH7.5 to remove unbound HIV pseudovirus and reproducible SERS spectra recorded as before. The recorded spectrum are then compared to a database of reference SERS spectra in order to confirm the identity of the captured viral pathogen.

In this Example, the oligoethylene glycol-terminated C11 SAM provides increased resistance to non-specific macromolecule adsorption onto the sensor surface, whilst the DNA aptamer provides specific recognition of gp120 proteins on the surface of the HIV pseudovirus; the combination of these enables the measurement of reproducible SERS spectra for the resultant aptamer-HIV pseudovirus complex, including where the HIV pseudovirus is captured by an aptamer from a blood or plasma sample obtained from a patient with suspected HIV infection.

As before, other in vitro selected anti-gp120 RNA aptamers that show sufficient affinity and specificity could be used in place of Aptamer 5, for example 5'-HS—(CH$_2$)$_6$-GGG AGG ACG AUG CGG ACA UAG UAA UGA CAC GGA GGA UGG AGA AAA AAC AGC CAU CUC UUG ACG GUC AGA CGA CUC GCC CGA-3' (SEQ ID NO: 7).[18]

6. Detection of Intact Bacterial Pathogens Using a DNA Aptamer-functionalised, SAM-derivatised SERS Sensor Surface DNA-functionalised, SAM-derivatised colloidal silver SERS sensor surfaces are prepared on screen printed electrodes essentially as described in Example 5, with the following amendment: an in vitro selected 5'-thio-anti-CFP10.ESAT6 DNA aptamer (Aptamer 6; e.g. CSIR2.11 or CSIR2.19 in reference 19) is used in place of the anti-Plasmodium falciparum lactate dehydrogenase DNA aptamer; as before, 1-mercaptoundecanyl-11-tri(ethyleneglycol) was used to form the back-filled SAM surrounding the immobilised DNA aptamer.

Figure 7:
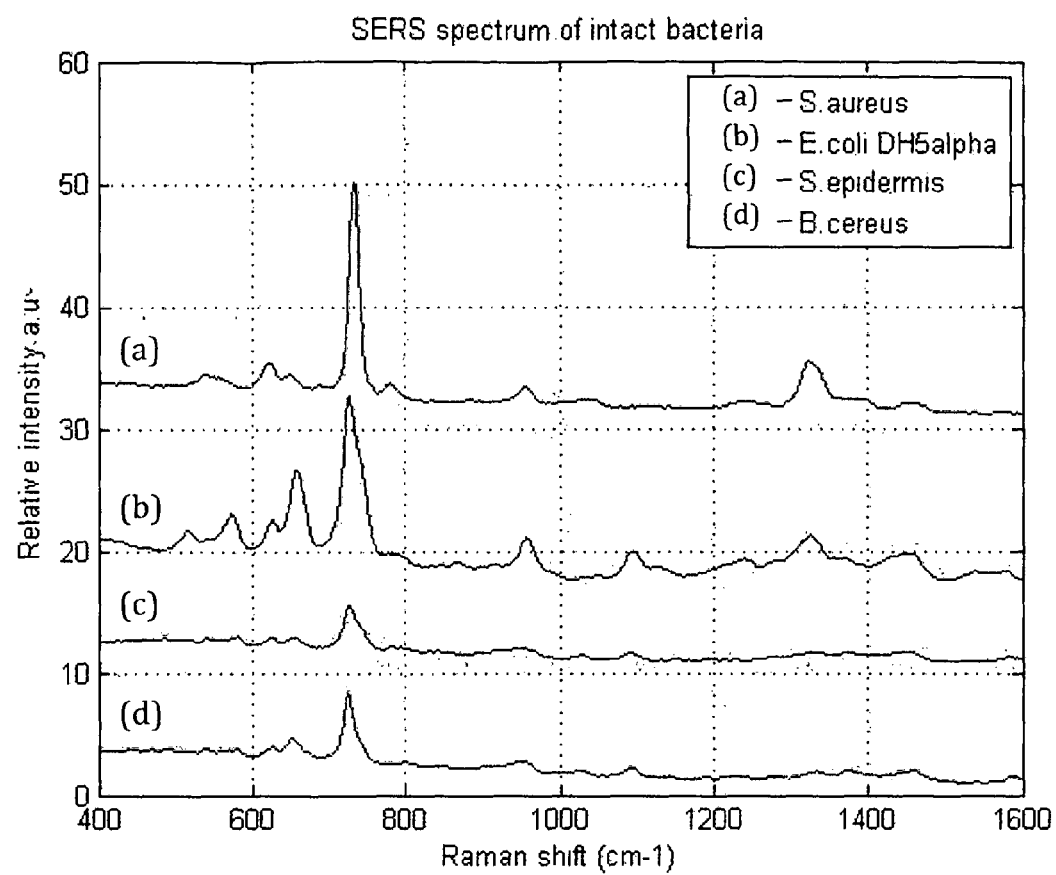
FIG. 7 shows offset reproducible SERS spectra acquired for differing live bacteria on an AgNP surface. These SERS spectra can be used to form a representative database of reference SERS spectra. (a) SERS spectrum for *S. aureus*; (b) SERS spectrum for *E. coli*; (c) SERS spectrum for *S. epidermis*; (d) SERS spectrum for *B. cereus*.
Figure 8:
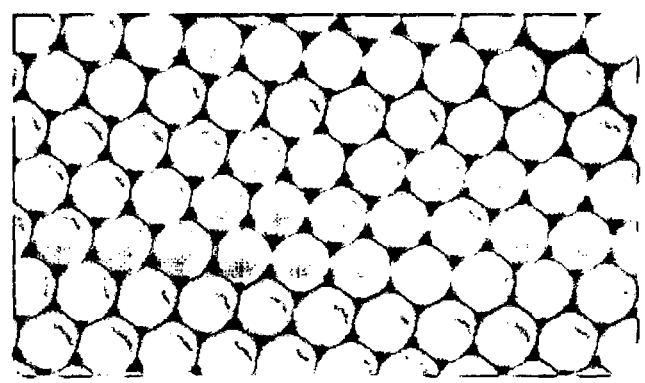
FIG. 8 is a scanning electron microscope (SEM) image of a typical AgFON surface.
Figure 9:
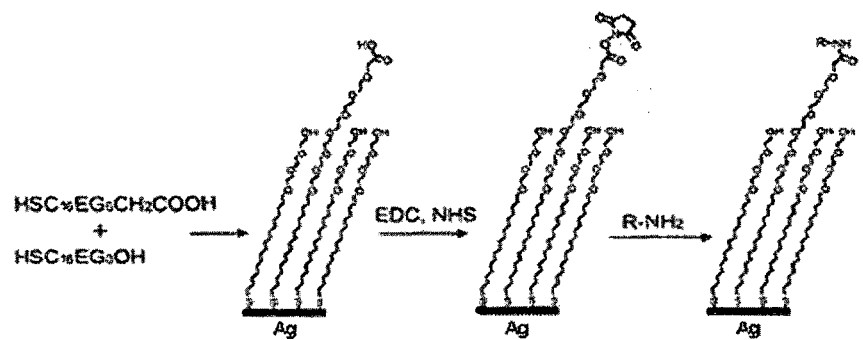
FIG. 9 is a schematic of formation of an aptamer-functionalised SAM on a silver surface (R—$NH_2$=5'-amino modified DNA aptamer).

A suspension of live *Mycobacterium tuberculosis* H37Rv (M. tb; 10$^6$ bacilli/ml) is incubated for 30 minutes on an Aptamer 6-functionalised, C11-EG3-SAM-derivatised AgNP surface, the surface then washed with 3×1 ml 10 mM HEPES pH7.5 to remove unbound M. tb and reproducible SERS spectra recorded as before. The recorded spectrum are then compared to a database of reference SERS spectra (see for example FIG. 7) in order to confirm the identity of the captured bacterial pathogen.

In this Example, the oligoethylene glycol-terminated C11 SAM provides increased resistance to non-specific macromolecule adsorption onto the sensor surface, whilst the DNA aptamer provides specific recognition of the CFP10.ESAT6 heterodimer present in the *Mycobacterium tuberculosis* cell wall; the combination of these enables the measurement of reproducible SERS spectra for the resultant aptamer-M.tb complex, including where the M.tb bacilli are captured by an aptamer from a liquified sputum sample obtained from a patient with suspected tuberculosis (TB) disease. Such a liquified sputum sample may contain up to ca. $10^4$ M.tb bacilli/ml depending on TB disease status and will also contain a mixture of other unidentified microorganisms (for example other actinomycetes such as non-tuberculous mycobacteria, or staphylococci such as *Staphylococcus aureus*) that may express an ESAT6 ortholog protein and which might therefore be cross-recognised by the anti-CFP10.ESAT6 aptamer;[19] those microorganisms can be distinguished from M.tb by comparison of the recorded SERS spectrum of the aptamer-analyte complex to a reference database, thus enabling discrimination between true and false positive results in a SERS assay of the invention for presence of M.tb bacilli in sputum.

7. Preparation of a DNA Aptamer-functionalised SAM-derivatised SERS Sensor Surface to Setect the Anaesthetic Propofol FIG. 8 shows a scanning electron microscope image of an AgFON surface prepared as described in Example 1. A mixed aptamer-functionalised SAM can then be formed on top of the AgFON surface as follows:

A 50:50 molar ratio mixture of carboxylic acid-terminated hexa(ethylene glycol)hexadecanethiol ($HSC_{16}EG_6CH_2COOH$) and tri(ethylene glycol)hexadecanethiol ($HSC_{16}EG_3OH$) is prepared at a final concentration 0.1 mg $mL^{-1}$ in dimethyl sulphoxide and incubated with the AgFON surface over night at room temperature to allow the SAM to form. The SAM-derivatised AgFON surface is then washed with de-ionised water followed by ethanol and dried under a stream of nitrogen. Activation of the carboxylic acid moiety of the SAM as an N-hydroxysuccinimide (NHS) ester is then performed by incubating the SAM-derivitised AgFON surface in a solution of 1-Ethyl-3-(3-dimethylaminopropyl) carbodiimide (EDC) and NHS (final concentrations 0.2M and 0.05M, respectively, in dry dimethylformamide) for 2 h, is then washed with de-ionised water followed by ethanol and dried under a stream of nitrogen.

An anti-propofol DNA aptamer is isolated by standard SELEX procedures[13] using an immobilised form of the anaesthetic compound propofol in the enrichment step. DNA synthesis is then used to create a a 5'-amino modified form of the anti-propofol DNA aptamer.

A 100 mM solution of a 5'-amino modified anti-propofol DNA aptamer is then incubated with the NHS-activated SAM-derivatised AgFON surface in phosphate buffered saline solution (pH 8.0) overnight at room temperature to allow amide bond formation between the 5'-amino modified anti-propofol DNA aptamer and the NHS-activated SAM. Finally, the aptamer-functionalised SAM formed on top of the AgFON surface is washed with de-ionised water followed by ethanol and dried under a stream of nitrogen. This process is depicted in FIG. 9.

8. Real Time Real Time Monitoring of the Blood Plasma Concentration of an Anaesthetic The following example describes an in vitro application of a SERS biosensor for a real-time monitoring of an anaesthetic, such as propofol. FIG. 12 shows an arrangement where the SERS biosensor is used for such an application. The SERS biosensor may be encapsulated in a device such as a flow cell (2). Blood is allowed to flow through the flow cell at a suitable flow rate (10-100 μl $min^{-1}$), controlled by a flow regulator (1). A device comprising a Raman spectrometer (3) with an integrated laser source, detector and associated optics as well as an embedded computer is placed over the flow cell that has an optical window to allow the excitation laser and resulting SERS signal to pass through, which is then detected by the Raman detector (3), processed in an on-board computer embedded in (3) and displayed in real-time on a monitor (4). When propofol binds to the anti-propofol aptamer, conformation change of the aptamer occurs. By monitoring the SERS signal of the aptamer-propofol complex in real-time and comparing the signal intensity to a standard curve, the concentration of propofol in blood can be determined with high accuracy. For this application, the aptamer-SAM partition layer must bind propofol reversibly such that at any given time the concentration of propofol close to the AgFON surface reflects, through establishment of dynamic equilibrium, the concentration of the analyte in the blood sample flowing through the sensor flow cell at that time. In addition, by comparison of the measured SERS spectrum to a database of reference SERS spectra, the identity of the measured analyte can be confirmed.

FIG. 13 shows the details of the flow cell and encapsulated SERS biosensor mentioned in the above example of a real time system to monitor anaesthetics. A single optical path couples the laser excitation to the biosensor and the SERS signal from the biosensor to the detector via an optical window on the flow cell. A notch filter centred at the excitation laser wavelength can reduce the backscattered laser excitation. A "head-on" arrangement is also possible where the excitation pathway is from the bottom of the flow cell and the SERS is detected from the top. Such an arrangement will have greater sensitivity. A typical portable Raman spectrometer system combines the laser excitation, associated optics, and detector into a single device.[16]

Instead of a flow cell, a micro-fluidic system can also be used where a micro-fluidic chip is attached to the SERS biosensor. The micro-fluidic system pumps a small volume of blood at the desired flow rate (e.g. 20 μl $min^{-1}$) over the SERS biosensor as shown in FIG. 14.

Another possible arrangement is to attach a SERS biosensor on a fibre optic cable as shown in FIG. 15. Such a fibre optic probe may be used to detect SERS by placing the probe directly into the medium (such as blood) to detect the analyte of interest.

REFERENCES

1. Dheda K, Davids V, Lenders L, et al (2010) PLoS ONE 5, e9848
2. Beeton-Kempen N, Shoko A & Blackburn J (2008) Pure & Applied Chemistry 80, 1793-1802.
3. Dieringer J A, McFarland A D, Shah N C, et al (2006) Faraday Discuss. 132, 9-26.
4. Haynes C L & Van Duyne, R P (2003) J. Phys. Chem. B 107, 7426-7433.
5. Wu D-Y, Ren B & Tian Z-Q (2006) Israel J. Chem. 46, 317-327.
6. Barbillon G, Bijeon J-L, Bouillard J-S, et al (2008) J. Microscopy 229, 270-274.
7. Wei W, Li S, Millstone J E et al (2009) Angew. Chem. 121, 4274-4276.
8. Meinhart C D, Piorek B, Lee S J, Moskovits M, Banerjee S & Santiago J G (2009) WO/2009/020479.
9. Shafer-Peltier K E, Haynes C L, Glucksberg M R & Van Duyne R P (2003) J. Am. Chem. Soc. 125, 588-593.
10. Lyandres O, Yuen J M, Shah N C, et al (2008) Diabetes Technol. Ther. 10, 257-265.
11. Cho H, Baker B R, Wachsmann-Hogiu S, et al (2008) Nanoletters 8, 4386-4390.
12. Huh Y S & Erickson D (2010) Biosensors and Bioelectronics 25, 1240-1243.

13. Khati M (2010) J. Clin. Pathol. 63, 480-487.
14. Neumann O, Zhang D et al (2009) Anal. Chem. 81, 10002-10006
15. Love J C, Estroff L A, Kriebel J K, Nuzzo R G & Whitesides G M (2005) Chem. Rev. 105, 1103-1169.
16. DeltaNu Raman systems, www.deltanu.com
17. Lee S, Song K-M, Jeon W, Jo H, Shim Y-B, Ban C (2012) Biosensors and Bioelectronics 35, 291-296.
18. Zhou J, Swiderski P, Li H, Zhang J, Neff C P, Akkina R, & Rossi J J (2009) Nucleic Acids Res. 37, 3094-3109.
19. Rotherham L S, Maserumule C, Dheda K, Theron J & Khati M (2012) Plos One 7, e46862.

The invention claimed is:

1. A method of identifying an analyte molecule in a biological sample, the method comprising the steps of:
capturing the analyte molecule onto a nano-structured silver SERS surface by means of an analyte molecule-specific aptamer, resulting in a specific aptamer-analyte molecule complex, which has a different pattern of Raman shifts in a SERS spectrum relative to a pattern for the aptamer or the analyte in isolation, the pattern of Raman shifts being unique and reproducible for the specific aptamer-analyte molecule complex, wherein amphiphilic molecules comprising an alkyl thio chain of at least 11 carbon atoms are attached to the silver surface to form a self-assembled monolayer (SAM), the SAM is coated with a layer of oligoethylene glycol molecules, and the analyte molecule-specific aptamer is attached directly to the SAM or attached directly to the silver surface and surrounded by the SAM,
obtaining SERS spectra at a plurality of different voltages;
measuring SERS signal intensity and unique pattern of Raman shifts for the specific aptamer-analyte molecule complex, and
comparing the measured SERS signal intensity and Raman shifts of a SERS spectrum measured for the specific aptamer-analyte molecule complex to a database of reference SERS spectra of aptamer-analyte molecule complexes wherein the database comprises two or more SERS spectra and wherein each SERS spectrum in said database is unique for a different aptamer-analyte molecule complex, thereby identifying the analyte molecule in the aptamer-analyte molecule complex.

2. The method of claim 1, further comprising comparing the measured SERS signal intensity of the specific aptamer-analyte molecule complex to a standard curve to quantify the abundance of the captured analyte.

3. The method of claim 1, further comprising confirming a true positive diagnostic result in a quantitative analyte assay on the biological sample if the measured Raman shifts of the SERS spectrum correspond to a reference spectrum for an aptamer-analyte complex of an analyte which is indicative of a disease or condition being diagnosed; or identifying a false positive result if the measured Raman shifts of the SERS spectrum correspond to a reference spectrum for an aptamer-analyte complex of an analyte which is not indicative of a disease or condition being diagnosed.

4. The method of claim 1, wherein the aptamer is a DNA aptamer.

5. The method of claim 1, wherein
the aptamer is attached directly to the silver surface and surrounded by the SAM.

6. The method of claim 5, wherein the aptamer is attached directly to the amphiphilic molecules of the SAM.

7. The method of claim 1, wherein the oligoethylene glycol molecules have exposed termini and are derivatised on the termini by the aptamer.

8. A method for diagnosing or quantifying an infection, disease or medical condition in a subject, comprising performing the method of claim 1 on a sample from the subject.

9. A method for monitoring a subject during anaesthesia, comprising performing the method of claim 1 on a sample from the subject.

* * * * *